United States Patent [19]

Mandalaywala et al.

[11] Patent Number: 4,574,734

[45] Date of Patent: Mar. 11, 1986

[54] UNIVERSAL ANIMAL ACTIVITY MONITORING SYSTEM

[75] Inventors: Ramakant H. Mandalaywala; Bogdan J. Zaleski, both of Columbus, Ohio

[73] Assignee: Omnitech Electronics, Inc., Columbus, Ohio

[21] Appl. No.: 614,063

[22] Filed: May 25, 1984

[51] Int. Cl.[4] .............................................. A01K 29/00

[52] U.S. Cl. .......................................... 119/1; 119/29

[58] Field of Search ...................................... 119/1, 29

[56] References Cited

U.S. PATENT DOCUMENTS

| | | | |
|---|---|---|---|
| 3,100,473 | 8/1963 | Kissel | 119/1 |
| 3,304,911 | 2/1967 | Hakata et al. | 119/29 X |
| 3,540,413 | 11/1970 | Castaigne | 119/1 |
| 3,965,865 | 6/1976 | Kundikoff | 119/19 |
| 3,974,798 | 8/1976 | Meetze, Jr. | 119/29 |
| 4,337,726 | 7/1982 | Czekajewski et al. | 119/1 |
| 4,448,150 | 5/1984 | Catsimpoolas | 119/1 |

OTHER PUBLICATIONS

An Arrangement for the Study of Fish Activity Using Photosensitive Devices. R. H. Mandalaywala et al., Oct., 1973.

An Automated Method for Studying Exploratory and Stereotyped Behaviour in Rats. Roger O. A. Makanjuola, et al. Psychopharmacology 1977.

*Primary Examiner*—Hugh R. Chamblee

*Attorney, Agent, or Firm*—Frank H. Foster

[57] ABSTRACT

An improved animal activity monitor of the type in which an animal is positioned in an arena having an array of two perpendicular sets of parallel light beams above the arena for detecting the animal position. In the improvement, transparent walls parallel to the beams subdivide the arena into areas, diagonally related ones of which may be used as subarenas for testing smaller animals. Each subarena has a unique pair of perpendicular beams which cannot be blocked by any other animal. The light beam array for each subarena is separately detected and processed in the manner formerly done for the entire arena. Individual switches associated with each arena or subarena or software routines to detect the presence and absence of an animal in each arena are used to enable or disable the collection of data from the arena or subarena. Each animal may be, in sequence, prepared and then inserted into the arena or subarena. Immediately after each animal is inserted into its arena or subarena, the collection of data for that animal is enabled until it is removed.

10 Claims, 8 Drawing Figures

38

40

34

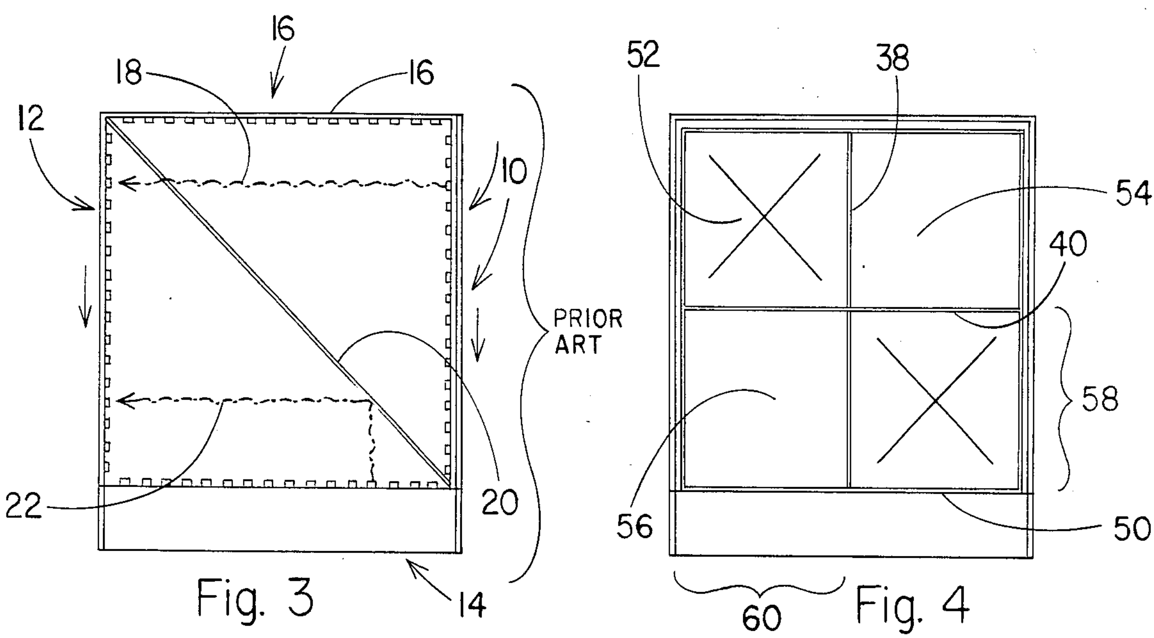
Fig. 3
Fig. 4
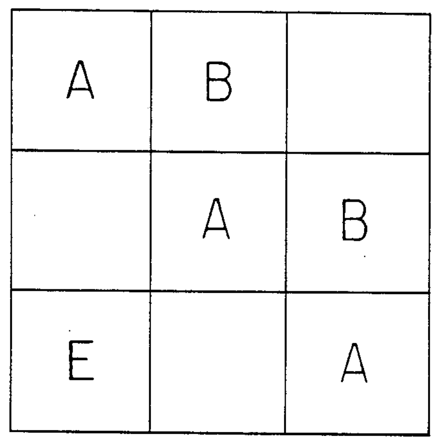
Fig. 5
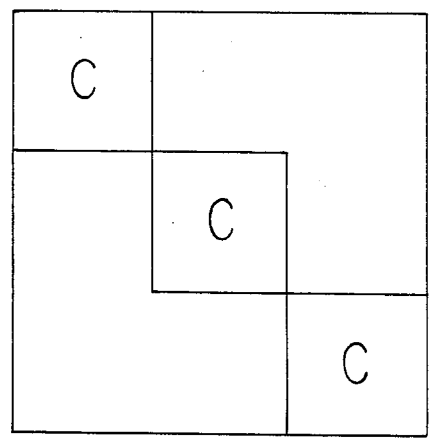
Fig. 6
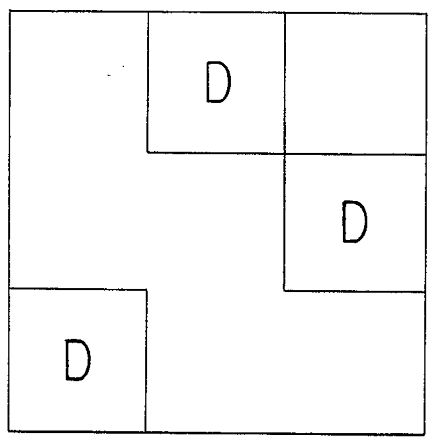
Fig. 7
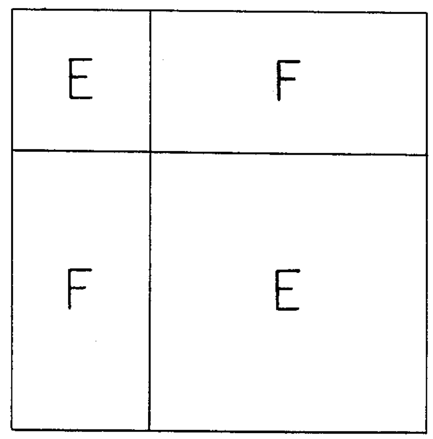
Fig. 8

UNIVERSAL ANIMAL ACTIVITY MONITORING SYSTEM

FIELD OF THE INVENTION

This invention relates generally to an apparatus for automatically monitoring scientific experiments and collecting data and more particularly relates to a device for confining laboratory animals and continuously detecting and processing data representing various types of animal movement.

BACKGROUND ART

It is often desirable to monitor the activity of laboratory animals, such as mice and rats, for scientific purposes. For example, a pharmaceutical company may wish to determine any changes in animal behavior resulting from the administration of a drug to that animal. This has conveniently been done with scientific equipment for continuously monitoring an animal's movement within a confined arena.

One useful device or system for detecting the animal's activity uses an array of two orthogonal sets of parallel light beams extending above the arena. One set of beam is radiated from a series of light sources mounted along one side of the arena. They travel parallel to the arena floor. Each beam of each set is radiated from a light source toward a series of associated light detectors on the opposite side of the arena. The second set of beams is created by similarly cooperating light sources along one of the remaining walls of the arena and light detectors along the opposite wall.

The light detectors are periodically scanned by data processing equipment to determine which light beam have been interrupted by the animal. From this an X and a Y coordinate in a set of rectangular coordinates can be determined and defines the instantaneous positions of the animal. The instantaneous position are recorded and totalized in accordance with known data collecting algorithms for experiments of this type. The circuitry, systems and data processing algorithms by which these X-Y positions are determined from the broken light beams and by which the X-Y positions are converted to the desired activity data is extensively discussed elsewhere in the techincal literature.

In the past, equipment having an arena of one size was manufactured for testing rats while equipment having a smaller arena was manufactured for testing mice. This meant that a laboratory wishing to test both rats and mice was required to purchase at least two different units, one of each size. Furthermore, if the laboratory was currently doing tests upon only one size of animal, then the equipment purchased for the other size animal sat idle.

It has been previously recognized that it would be desirable to construct an animal activity monitor system which, with only slight modification and slight additional cost, can be adapted for use with either mice or rats.

One prior art attempt to do this is illustrated in FIG. 3. FIG. 3 shows an arena with a first set of light sources 10 aimed toward a first set of light detectors 12 along with a second set of light sources 14 aimed toward a second set of light detectors 16. In ordinary use for monitoring the activity of each rat, each light beam, such as light beam 18, is directed entirely across the arena to a detector upon the opposite side in the conventional manner.

However, in an attempt to permit use of the same equipment for mice, a diagonal, doubly reflective partition 20 was inserted across the center of the arena. The idea was that a light beam from a light source, such as light beam 22, would then be reflected by the central partition 20 to a detector along the side adjacent to the light sources. In this manner each of the two halves of the arena has its own detection system comprising a series of sources and a series of detectors. It was then a simple manner to modify the data processing software to coordinate each light source with its associated light detector to derive data indicating which light beams the animal was blocking.

There are two major problems, however, with this system. First, in practical systems it is very difficult and impractical to form the central partition 20 in appropriate, precise alignment so that all of the light beams from each of the sources along the side 14, for example, would be aimed upon their associated detectors, such as the detectors 12. Furthermore, the data which is obtained in essentially one dimensional in that the only information which can be obtained is that an animal is somewhere in the light beam. Because there are no longer two sets of transverse light beams, no determination can be made exactly where along the reflected light beam the animal is positioned. Therefore, the data derived was reduced to a single parameter of study and X and Y position coordinates became impossible to obtain in this system.

There is therefore a need for a manner in which a test arena can be inexpensively modified so that it may be converted from the testing of larger animals to the testing of smaller animals and which nonetheless can provide instantaneous X and Y position coordinates.

It is also known in prior art systems to connect a multiplicity of test arenas, each with its own orthogonal sets of parallel light beams, to a single data processing computer. In the normal use of such prior art equipment, the animals are first all prepared. When all the animals have been placed in the appropriate arena, operation of the data processing equipment is begun.

This system, however, introduces an error in the test data or causes valuable test data to be lost or both. The reason is that it takes time to prepare each of several animals, for example by injecting them with a drug, and to then place them in the arena. There may, therefore, be a significantly longer time delay from the time the first animal is prepared until the time the last animal is prepared. Since the collection of data for all animals is begun immediately after the last animal is prepared, the time delay from preparation to data collection is different for each animal. This difference may in fact be 2 to 3 minutes. Such a time lag can be very significant particulary in experiments that may last only a short time, such as 2 to 3 minutes. For example, the testing scientist may wish to determine the animal's exploratory activity during its habituation period, the time during which the animal is becoming acquainted with the new environment of the arena. A 2 or 3 minute delay from preparation of some animals to initiation of data collection for that animal will give invalid or erroneous data for the first animals with such a prior art system.

There is therefore a need for an animal activity monitoring system which can preserve the desirable arrangement in which several arenas are connected to a single data processing system, but which can permit all tested animals to be given a uniform time delay after preparation. In this manner all animals would be tested under the same conditions so that the data representing their activity is more accurate and reliable.

Most testing laboratories need to study as many animals as they possibly can in the shortest time possible so that they may obtain a sufficiently large amount of data to be statistically significant. Thus, the faster and more reliably accurate the animal test can be processed, the better and more economical is the system.

SUMMARY OF THE INVENTION

In the present invention an arena having two transversely oriented sets of parallel light beams is subdivided into a plurality of subarenas by light transmitting walls which extend across the arena parallel to the light beams. These walls may be formed of transparent wall material which will permit the light beams to travel through them sufficiently undiffused so that each light beam will continue to be incident upon the same light detector as it is incident upon when the entire arena is used for a single animal, without the presence of any subdiving walls. Each of the subarenas which may be used are laterally offset from each of the other subarenas so that each light beam intersects only a single subarena. For each subarena those and only those light beams which pass through that subarena are separately detected and processed in the same manner as is conventionally done for an entire single arena. Each subarena therefore has two transverse sets of parallel light beams which may be detected independently of the transverse sets of parallel light beams for each other subarena.

BRIEF DESCRIPTION OF THE DRAWINGS

FIG. 3 illustrates a prior art attempt to subdivide an animal activity arena.

FIGS. 4–8 illustrate a variety of alternative embodiments of the invention showing different ways that a main arena may be subdivided.

Figure 1:
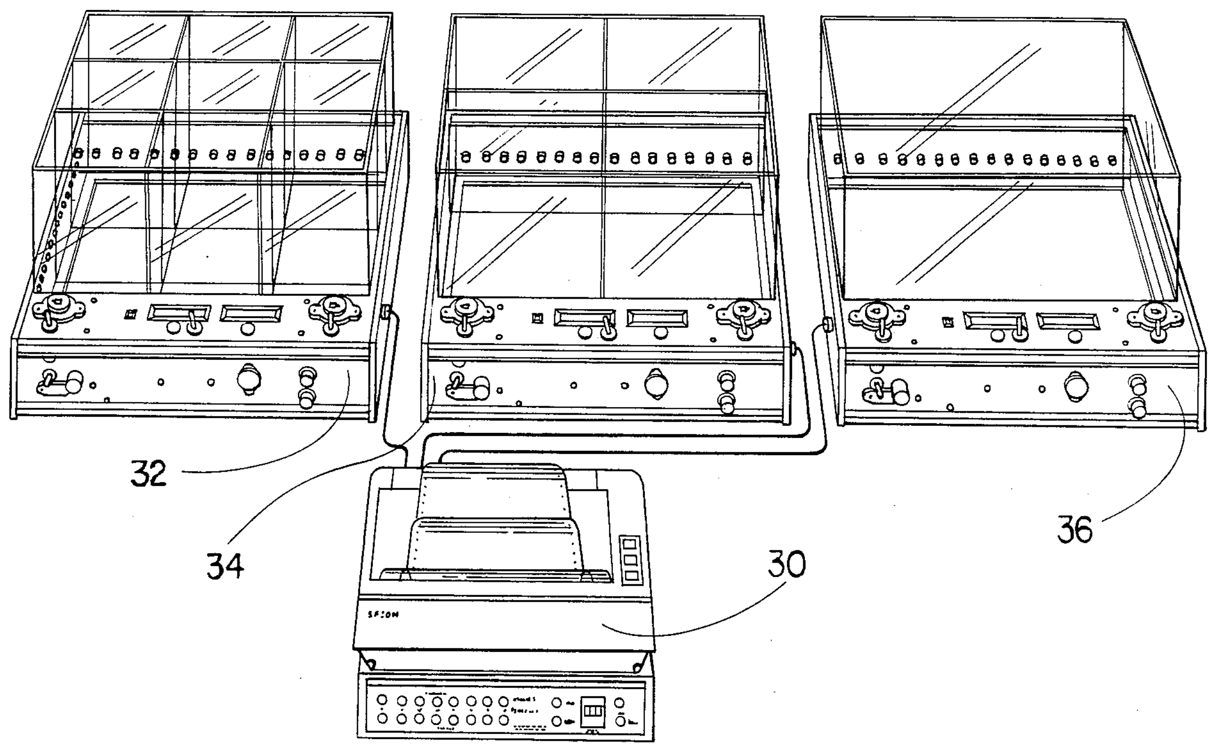
FIG. 1 illustrates several animal testing arenas connected to a single data processing system and also illustrates different manners of subdividing these arenas in accordance with the present invention.

In describing the preferred embodiments of the invention which is illustrated in the drawings, specific terminology will be resorted to for the sake of clarity. However, it is not intended that the invention be limited to the specific terms so selected and it is to be understood that each specific term includes all techincal equivalents which operate in a similar manner to accomplish a similar purpose.

DETAILED DESCRIPTION

FIG. 1 illustrates data processing equipment 30 which is connected by appropriate electrical cables to animal activity arenas 32, 34 and 36. For purposes of illustration arena 36 is undivided, arena 34 is subdivided into four areas, two of which are useful as subarenas, and arena 32 is subdivided into six areas, three of which are useful as subarenas.

Figure 2:
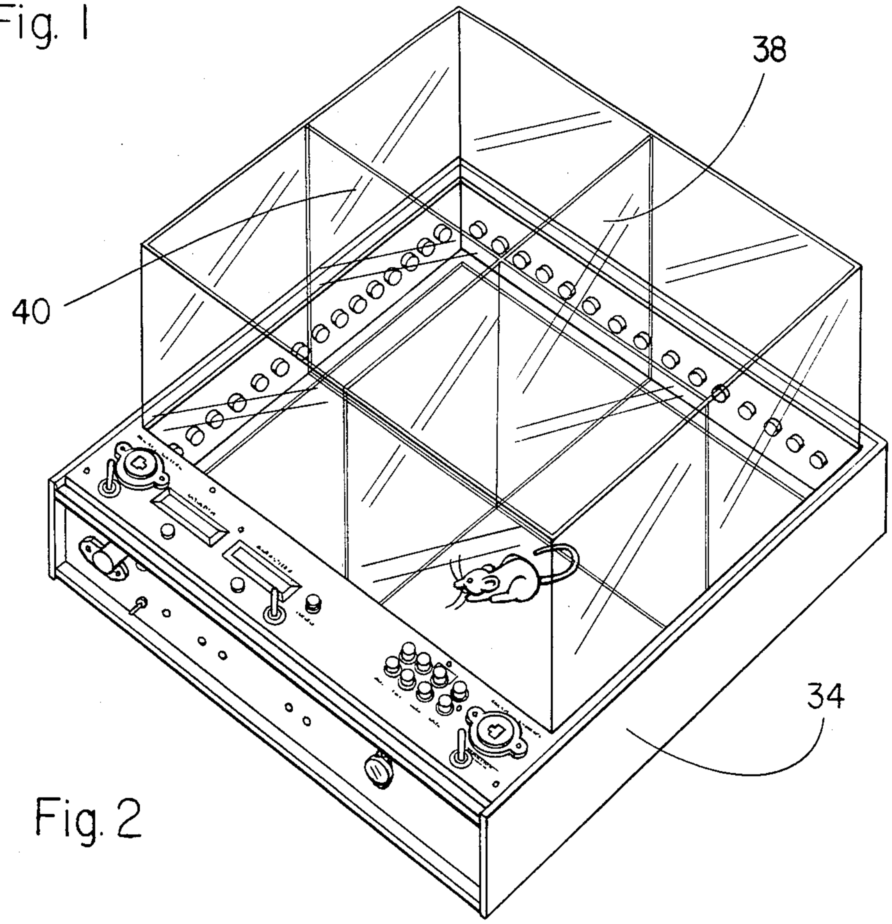
FIG. 2 illustrates in perspective the detail of an animal activity arena which is subdivided in accordance with the present invention.

FIG. 2 illustrates in detail the arena 34. The arena 34 is identical to the arena 36 of FIG. 1 except that a pair of wall inserts 38 and 40 have been placed within the arena to divide it into four equal areas. The arena 34 has light sources and associated detectors positioned as described above in connection with FIG. 3. Preferably, the beams are spaced upon 1" centers and there are 16 beams along each outer arena wall. The walls 38 and 40 must be sufficiently transparent that light can travel from each light source, across the arena and impinge upon its associated light detector. For example, clear plastic such as Lucite may be used. The walls 38 and 40 are positioned parallel to the light beams and are desirably positioned intermediate the two central beams of each set of parallel beams.

FIG. 4 is a top diagrammatic view of the embodiment of FIG. 2. Although the main arena is subdivided by the walls 38 and 40 into four areas, only two areas may be used. They are either set of two subarenas which are laterally offset from each other so that each of the light beams intersects only a single subarena. Thus, areas 50 and 52, marked with a large X, may be selected as unused areas while areas 54 and 56 may be selected as the subarenas which may be used for testing smaller animals.

Each subarena therefore has two orthogonal sets of eight parallel light beams. For example, subarena 56 has light beams from sources 58 and light beams from sources 60. These light beams represent X and Y coordinate detecting beams. Subarena 54 therefore has an $8\times8$ array for that subarena. The subarena 54 also has a similar $8\times8$ array of entirely different beams. Each array is separately detected for each subarena and therefore data for each subarena is separately processed. However, each $8\times8$ array is processed in the same manner as the other $8\times8$ array. Also, each is processed with the same algorithms as a $16\times16$ array uses for the whole arena if the walls 38 and 40 are removed so that the arena may be used for larger animals.

The arena may be subdivided into more and smaller areas. The useful subarenas may then be chosen as described above so that the X and Y beams for each subarena will not be blocked by an animal in another subarena. The subarenas are chosen so that no animal is capable of breaking a beam which is assigned to another animal. No animal may be allowed in the beam shadow of another. It can therefore be seen that the useful arenas are diagonally related, but some variations may be chosen.

FIG. 5, for example, illustrates that the main arena may be subdivided into 9 areas, three of which will be useful as subarenas. For example, the subarenas marked A along a diagonal of the arena may be used, or, in the alternative, for example, the subarenas B may be used. Each set of subarenas meets the above described criteria.

FIGS. 6 and 7 illustrate that it is not necessary to extend the transparent walls entirely around the unused areas. For example, if the three areas labelled C in FIG. 6 are chosen as the animal testing subarenas, only those subarenas need be bounded by the transparent walls.

Similarly, in FIG. 7 if the subarenas B are chosen the walls may be limited as shown in FIG. 7.

Illustrated in FIG. 8 is the fact that the subarenas are not necessarily of the same size or dimensions. The small and large arena pair E and F may be used. Each will be covered by an array of transverse parallel beams. Alternatively, two elongated, rectangular subarenas labelled F may be used.

Although subdividing the arena into smaller subarenas means fewer beams in the array for each subarena, the beams remain the same distance apart and are unchanged and therefore the resolution of the system for the subarenas remains identical to the resolution for the large arena.

Further subdivision may be made into more and smaller subarenas so that the present invention permits a single arena to be used for large animals, such as rats or guinea pigs, intermediate size animals, such as mice, and even for insects.

Although the systems of analyzing the data from the light beam arrays is well known in the art, a brief description of the system may be more convenient than references to the particular art. Utilizing known software techniques, the light beam detectors for each of the two parallel sets of beams are scanned to determine which of the beams are blocked. A position which is central to all of the blocked light beams is determined and assigned as the X or Y coordinate as is appropriate for whichever set is being detected.

We prefer to sample the array 100 times per second so that for each 100th of a second there is a set of X, Y coordinates which define the instantaneous position of the animal. Changes in the X, Y position are then data processed in the manner well known in the art.

In order to obtain uniform equivalent data for each animal being tested, a manually operated switch is associated with each arena or subarena being used. The switch is electrically connected in a well known manner for disabling and enabling the processing of data from its associated arena or subarena. This switch may, for example, be a simple make/break switch in the data connection line to the data processing system or it may be a switch for connecting an input port of the data processing system to a high or low voltage to signal whether or not data should be accepted from the particular arena or subarena associated with the switch.

This permits staggered starting times for the animals. Each animal may be individually prepared for the test, put in the arena or subarena and then the switch for that arena is actuated to initiate or enable the processing of data for that animal. The next animal is then prepared, placed in its arena and the switch operated to enable the taking of data for that animal. This process is repeated until all animals have been prepared. The data, however, is analyzed from a time delay following the preparation of the animal for the test.

As an alternative to the use of the manual switch the same advantages can be accomplished by designing the software to detect whether no light beams are broken. For example, a simple software subroutine can be prepared which interrogates all the light detectors of at least one of the two sets of detectors making up the array. When no light beams are blocked, then no animal is present in the arena and therefore the processing of data is disabled.

Immediately upon the insertion of an animal, the subroutine detects the blockage of a light beam indicating that an animal is present and in response to that initial light beam blockage, enables the collection of data.

Similarly, the subroutine may alternatively be constructed so that, upon removal of the animal from the arena and the resulting detection that no light beams are blocked, the processing of data is again disabled. In this manner the collection of the data for an animal inserted in an arena or in a subarena is begun immediately upon the insertion of the animal and is halted immediately upon withdrawal of the animal.

The principles of the present invention are also applicable to monitoring systems which are capable of monitoring vertical movement by an animal. For example, the testing scientist may wish to know how often and where an animal stands upon its hind legs. This may be accomplished in a conventional manner by providing a third set of parallel light beams spaced above the array of the first two sets. When any of these beams are broken the monitoring system detects that an animal has raised to that height and the lower array determines the animal position as described above.

From the above description it can be seen that the improvement of the present invention requires only two simple and inexpensive modifications to existing animal activity monitoring systems. First, the inexpensive transparent walls subdividing an arena are inserted in the arena. Secondly, the software must be modified to separately determine X and Y coordinates from each of two sets of transverse beams which are uniquely associated with a single subarena. Aside from those modifications both the hardware and the software remain as found in the prior art.

As an improvement a mechanical switch or corresponding software routines can also be used to disable and enable the collection of data in order to permit data to be collected under uniform circumstances.

While certain preferred embodiments of the present invention have been disclosed in detail, it is to be understood that various modifications in its structure may be adopted without departing from the spirit of the invention or the scope of the following claims.

We claim:

1. An improved animal activity monitor of the type wherein the position of an animal within an enclosure of substantially rectangular walls defining an arena is detected by an array of transversely oriented sets of parallel light beams above a floor of said arena to be broken by an enclosed animal, each beam being radiated from a light source and directed toward an associated detector, wherein the improvement comprises:

an insert means of transparent walls for transmitting said light beams through the walls, some of said walls being oriented parallel to each of said sets of parallel beams, said transparent walls subdividing the arena into subarenas, each of said subarenas being laterally offset horizontally and longitudinally from the other subarenas so that each of said light beams intersects only a single subarena, whereby animals are placed in subarenas that are in staggered and diagonally apart relationship.

2. A animal activity monitor in accordance with claim 1 wherein said beams and said walls are orthogonal.

3. An improved animal activity monitoring apparatus in accordance with claim 1 wherein said apparatus further includes data processing means connected to said light detectors and at least one manually operated switch associated with each of said arenas for selectively enabling and disabling the processing of data from its associated arena.

4. An apparatus in accordance with claim 3 wherein a manually operated switch is associated with each of said subarenas for selectively enabling and disabling the processing of all experiment data from its associated subarena.

5. An improved animal activity monitor in accordance with claim 1 which further includes:

(a) data processing means connected to said light detectors;

(b) means for disabling the processing of all experiment data from the arena; and (c) means for enabling the processing of all experiment data for the arena immediately following the placement of an animal in the arena.

6. An apparatus in accordance with claim 5 wherein said means comprises a mechanical switch interposed in the conductors between said monitoring apparatus and said computer.

7. An apparatus in accordance with claim 5 wherein said enabling and disabling means more specifically comprises:

(a) means for detecting the absence of an animal from the arena;

(b) means for disabling the processing of all experiment data from said monitoring apparatus when said animal's absence is detected;

(c) means for detecting the insertion of an animal in the arena; and (d) means for initiating the processing of all experiment data in response to the insertion of said animal.

8. A method for converting a single-animal, animal activity monitor of the type having an enclosure of substantially rectangular walls and a floor and having transversely oriented sets of parallel light beams above the floor to be broken by an enclosed animal, to a multi-animal, animal activity monitor without requiring the addition of more light beams, the method comprising:

(a) subdividing the arena into a plurality of subarenas by positioning between the subarenas light transmitting walls which are parallel to the light beams, each subarena being laterally offset horizontally and longitudinally from each other subarena so that each light beam intersects only a single subarena;

(b) placing animals in subarenas that are in staggered and diagonally apart relationship;

(c) separately detecting for each subarena only the light beams which pass through that subarena; and (d) separately processing the detected data for each subarena.

9. A method in accordance with claim 3 further comprising the steps of:

(a) disabling the processing of all experiment data from all subarenas; and (b) enabling the processing of all experiment data for each subarena immediately after placing an animal in the subarena.

10. A method in accordance with claim 9 wherein said method further comprises the step of detecting the absence of the blockage of any light beams of at least one set of beams and enabling said processing of experiment data in response to the initial blockage of one of said light beam.

* * * * *